(12) United States Patent
Mau et al.

(10) Patent No.: US 8,013,213 B2
(45) Date of Patent: Sep. 6, 2011

(54) GUAYULE PLANTS, PRODUCTS, AND DERIVATIVES

(75) Inventors: Christopher J. D. Mau, Pullman, WA (US); Katrina Cornish, Vista, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 1352 days.

(21) Appl. No.: 11/285,918

(22) Filed: Nov. 23, 2005

(65) Prior Publication Data

US 2006/0217512 A1 Sep. 28, 2006

Related U.S. Application Data

(60) Provisional application No. 60/630,909, filed on Nov. 24, 2004.

(51) Int. Cl.
*C12N 15/82* (2006.01)
(52) U.S. Cl. ....................................... 800/288
(58) Field of Classification Search ........................ None
See application file for complete search history.

(56) References Cited

U.S. PATENT DOCUMENTS 6,316,695 B1 11/2001 Han et al.

OTHER PUBLICATIONS

Veatch, M. et al. Association for the Advancement of Industrial Crops Conference Abstracts Published Oct. 12, 2003 p. 1.*
Veatch M. et al. Industrial Crops and Products vol. 22 (2005) pp. 65-74.*

Garbarino, J.E. and Belknap, W.R., "Isolation of a ubiquitin-ribosomal protein gene (ubi3) from potato and expression of its promoter in transgenic plants," Plant Molecular Biology (1994) 24:119-127.
Jones, J.D.G. et al., "Effective vectors for transformation, expression of heterologous genes, and assaying transposon excision in transgenic plants," Transgenic Research (1992) 1:285-297.
Koyama, T. et al., "Thermostable Farnesyl Diphosphate Synthase of *Bacillus stearothermophilus*: Molecular Cloning, Sequence Determination, Overproduction, and Purification," J. Biochem (1993) 113 (3):355-363.
McBride, K.E., and K.R. Summerfelt, "Improved binary vectors for Agrobacterium-mediated plant transformation," Plant Molecular Biology (1990) 14:269-276.
Ohnuma, S., M. Suzuki, and T. Nishino, "Archaebacterial Ether-linked Lipid Biosynthetic Gene," Journal of Biological Chemistry (1994) 269(20):14792-14797.
Ohnuma, S., et al., "Conversion of Product Specificity of Archaebacterial Geranylgeranyl-diphosphate Synthase," Journal of Biological Chemistry (1996) 271(31):18831-18837.

* cited by examiner

*Primary Examiner* — Russell Kallis
(74) *Attorney, Agent, or Firm* — Elizabeth R. Sampson; Margaret A. Connor; John D. Fado (57) ABSTRACT

Transgenic guayule lines were created by constitutively expressing transgenes that encode for prenyltransferase and allylic diphosphate synthase. These new lines are important to rubber production because they result in plants that produce latex rubber which is lower in guayulin, a compound that produces a skin irritation in some animals. Controlling prenyltransferase production also permits the control of the production of resin by the plants, which has important industrial implications. Additionally, prenyltransferase manipulation can result in latex particles of different size, containing rubber of different molecular weight, which is also significant to industrial production. Although the elevated prenyltransferase activity in the transgenic lines resulted in shorter rubber molecules, the number of rubber molecules made by these transgenic lines was increased.

12 Claims, 11 Drawing Sheets

GUAYULE PLANTS, PRODUCTS, AND DERIVATIVES

UTILITY PATENT APPLICATION

This is a utility patent application, filed pursuant to 35 U.S.C. §111(a).

CLAIM OF PRIORITY

This application relates to and claims the filing date of U.S. Provisional Application No. 60/630,909, filed on Nov. 24, 2004.

BACKGROUND OF THE INVENTION

1. Field of the Invention

The present invention relates to the enhanced production of latex rubber from the guayule plant, a desert shrub that is native to northern Mexico and the southwestern United States.

2. Description of the Art

World-wide consumption of natural rubber was 6.6 million metric tons in 1998, with the US importing over $10 billion worth of raw material and finished rubber goods. Currently the only commercially harvestable source of natural rubber is a tropical plant, *Hevea brasiliensis*. Because the genetic stock of this crop plant is very narrow and the growing range of the plant is limited to the tropics, other sources of natural rubber have been sought during the last century. One such plant that has been studied extensively during this time is *Parthenium argentatum* Gray (guayule).

Guayule is a perennial, indigenous to the Chihuahuan desert of northern Mexico (Lloyd, 1911) and southwestern U.S., that produces rubber during the late fall and winter months (Cornish and Siler, 1996). It is currently being developed as a new industrial crop because it promises to be the source of high quality natural rubber which also happens to be hypoallergenic (Carey et al. 317-20; Siler, Cornish, and Hamilton 895-902). Current breeding efforts to increase rubber yield in this plant have raised the level of rubber yield to about 10% dry weight (Estilai and Ray, in Whitworth and Whitehead). The biochemical pathways of the plant have also been the subject of extensive investigation. (Bonner and Arreguin (1949), Benedict (1983), Cornish (1993), Cornish and Siler (1995), Castillón and Cornish (1999)).

The synthesis of natural rubber involves the polymerization of thousands of molecules of isopentenyl diphosphate added to an allylic diphosphate initiator (usually assumed to be farnesyl diphosphate). Rubber biosynthesis represents an offshoot of terpenoid metabolism in the plants that produce it and occurs outside the plastid on cytoplasmic vesicles contained by a lipid monolayer (Cornish, Wood, and Windle 85-96). The formation of this secondary metabolite occurs within a symplastic laticifer in *Hevea brasiliensis* and within the bark parenchyma cytoplasm of *P. argentatum* (Backhaus 283-93). The absence of laticifers in the rubber synthesis in *P. argentatum* makes this plant a simpler model than *H. brasiliensis* to study the regulation of natural rubber production in vivo. In addition, *P. argentatum* produces a resin rich in sesquiterpene- and triterpene-derived components (Schloman, Jr. et al. 873-76), which may possess promising industrial uses and whose content might be influenced by manipulating the terpenoid pathway.

Manipulating the levels of substrates that can be used by the rubber transferase in the terpenoid biosynthetic pathway, therefore, should result in increased yield or improved quality of latex rubber. One such target in the metabolic pathway involves the allylic diphosphate initiators.

Manipulating the levels of substrates that can be used by the rubber transferase also should result in increased yield of the resin components produced by the terpenoid biosynthetic pathway.

SUMMARY OF THE INVENTION

The instant invention involves the genetic manipulation of guayule plants which results in an increased level of allylic diphosphate initiators as well as enhanced activity of prenyltransferase. Both are indicators of enhanced rubber synthesis.

Guayule plants were transformed to express constitutively heterologous allylic diphosphate synthases in the cytosol. The transformed plants were propagated vegetatively, transplanted from the laboratory into the field, and analyzed for two growing seasons.

The transformation resulted in guayule containing reduced amounts of rubber contaminants such as guayulins, and producing enhanced levels of other valuable guayule plant products such as resin.

BRIEF DESCRIPTION OF THE DRAWINGS

FIG. 1 is a chemical diagram showing terpenoid metabolism in the transgenic *Parthenium argentatum* plants discussed in this disclosure. IPP is the abbreviation for isopentenyl diphosphate. OPP represents an oxygen atom linking the diphosphate group to the carbon atom from the allylic terpenoid backbone. FPP is the abbreviation for farnesyl diphosphate synthase. GGPP is the abbreviation for geranylgeranyl diphosphate synthase. Gexaprenyl-PP is the abbreviation for gexaprenyl diphosphate. Heptaprenyl-PP is the abbreviation for heptaprenyl diphosphate. The dotted bond in the rubber molecule indicates that the initiator substrate is not limited to the FPP shown in the molecule. The dotted arrow represents the enzymatic steps to achieve the shown structure. If R=cinnamoyl, then the structure represents guayulin A; if R=p-methoxybenzoyl, then the structure represents guayulin B.

FIG. 2A shows the transformed line N4-2 iota, compared to the control line NC beta. FIG. 2B shows transformed lines A1-4 epsilon and A4-4 alpha, and are compared to the control lines AC beta, AC delta, AC epsilon and AC zeta.

FIG. 3A shows transformed lines N4-2 iota and is compared to the control line NC beta. FIG. 3B shows transformed lines A1-4 epsilon and A4-4 alpha, and are compared to the control lines AC beta, AC delta, AC epsilon and AC zeta.

DEFINITIONS

A1-4 epsilon refers to a line created by transforming the *Parthenium* hybrid cultivar AZ101 with the pCM1 binary plasmid containing the T-DNA expressing the *Bacillus stearothermophilus* farnesyl diphosphate synthase regulated by the constitutive cauliflower mosaic virus 35S promoter. This line produces increased cytosolic levels of farnesyl diphosphate, which can be utilized by the guayule rubber transferase, as well as enzymes involved in resin and guayulin production.

A4-4 alpha refers to a line created by transforming the *Parthenium* hybrid cultivar AZ101 with pCM4 binary plasmid containing the T-DNA expressing *Sulfobolus acidocaldarius* mutant geranylgeranyl diphosphate synthase regulated by the constitutive potato ubi3 promoter. This line produces increased cytosolic levels of hexa- and heptaprenyl diphosphate, which can be utilized by the guayule rubber transferase.

AC beta refers to a line created by transforming the *Parthenium* hybrid cultivar AZ101 with the *Agrobacterium* binary plasmid pCGN1547 containing the T-DNA lacking an allylic diphosphate synthase. This line is a control for comparison to A1-4 epsilon and A4-4 alpha.

AC delta refers to a line created by transforming the *Parthenium* hybrid cultivar AZ101 with the *Agrobacterium* binary plasmid pCGN1547 containing the T-DNA lacking an allylic diphosphate synthase. This line is a control for comparison to A1-4 epsilon and A4-4 alpha.

AC epsilon refers to a line created by transforming the *Parthenium* hybrid cultivar AZ101 with the *Agrobacterium* binary plasmid pCGN1547 containing the T-DNA lacking an allylic diphosphate synthase. This line is a control for comparison to A1-4 epsilon and A4-4 alpha.

AC zeta refers to a line created by transforming the *Parthenium* hybrid cultivar AZ101 with the *Agrobacterium* binary plasmid pCGN1547 containing the T-DNA lacking an allylic diphosphate synthase. This line is a control for comparison to A1-4 epsilon and A4-4 alpha.

N3-1 alpha and N3-2 alpha refer to lines created by transforming the *Parthenium argentatum* cultivar N6-5 with the *Agrobacterium* binary plasmid pCM3 containing the T-DNA expressing a *Sulfobolus acidocaldarius* geranylgeranyl diphosphate synthase (Ohnuma et al., 1998) regulated by the constitutive potato ubi3 promoter. These lines produce increased cytosolic levels of geranylgeranyl diphosphate, which can be utilized by the guayule rubber transferase.

N4-2 iota, N4-2 lambda, N4-2 xi and N4-2 pi refer to lines created by transforming the *Parthenium argentatum* cultivar N6-5 with the *Agrobacterium* binary plasmid pCM4 containing the T-DNA expressing a mutated *Sulfobolus acidocaldarius* geranylgeranyl diphosphate synthase (Ohnuma et al., 1998) regulated by the constitutive potato ubi3 promoter. These lines produce increased cytosolic levels of hexa- and heptaprenyl diphosphate, which can be utilized by the guayule rubber transferase.

N4-4 beta, N4-4 gamma and N4-4 epsilon refer to lines created by transforming the *Parthenium argentatum* cultivar N6-5 with the *Agrobacterium* binary plasmid pCM4 containing the T-DNA expressing a mutated *Sulfobolus acidocaldarius* geranylgeranyl diphosphate synthase (Ohnuma et al., 1998) regulated by the constitutive potato ubi3 promoter. These lines produce increased cytosolic levels of hexa- and heptaprenyl diphosphate, which can be utilized by the guayule rubber transferase.

NC beta refers to a line created by transforming the *Parthenium argentatum* cultivar N6-5 with the *Agrobacterium* binary plasmid pCGN1547 containing the T-DNA lacking an allylic diphosphate synthase. This line is a control for comparison to N4-2 iota, N4-2 lambda, N4-2 xi and N4-4 beta.

Guayule line N6-5 refers to the *Parthenium argentatum* line N6-5.

Guayule line AZ101 refers to the *Parthenium* hybrid resulting from a cross of *Parthenium argentatum* and *Parthenium tomentosum*. This hybrid produces a greater biomass during the growing season compared to other pure breeding *Parthenium argentatum* cultivars.

Binary vector pCM1 refers to the binary plasmid derived from pCGN1547 and containing the *Bacillus stearothermophilus* FPP synthase cDNA regulated by the cauliflower mosaic virus 35S promoter and has been deposited with the Agricultural Research Service Culture Collection (NRRL) assigned accession number NRRL B-30799.

Binary vector pCM3 refers to the binary plasmid derived from pCGN1547 and containing the GGPP synthase cDNA (from *Sulfobolus acidocaldarius*) regulated by the promoter from the potato ubiquitin UBI3 gene and has been deposited with ATCC the Agricultural Research Service Culture Collection (NRRL) assigned accession number NRRL B-30800.

Binary vector pCM4 refers to the binary plasmid derived from pCGN1547 and containing the L4 mutant GGPP synthase cDNA (from *Sulfobolus acidocaldarius*) regulated by the promoter from the potato ubiquitin UBI3 gene and has been deposited with the Agricultural Research Service Culture Collection (NRRL) and assigned accession number NRRL B-30801.

NPTII is a selectable marker gene whose sequence has been recorded at Genebank, Accession No. U00004.

IPP refers to isopentenyl diphosphate, the substrate used by rubber transferase to elongate the rubber molecule present in the catalytic site of the enzyme.

FPP synthase refers to farnesyl diphosphate (FPP) synthase, which catalyzes the condensation between isopentenyl diphosphate and geranyl diphosphate to yield farnesyl diphosphate.

GGPP synthase refers to geranylgeranyl diphosphate (GGPP) synthase, which catalyzes the condensation between isopentenyl diphosphate and farnesyl diphosphate to yield geranylgeranyl diphosphate.

Mw is defined as the weight average molecular weight and is calculated by $\Sigma(n_i M_i^2)/\Sigma(n_i M_i)$. Mn is called the number average molecular weight and is calculated by $\Sigma(n_i M_i)/\Sigma n_i$. Mz is known as the high molecular weight moment and is calculated by $\Sigma(n_i M_i^3)/\Sigma(n_i M_i^2)$. In these formulas, ni is the number of molecules with molar mass Mi.

DETAILED DESCRIPTION OF THE INVENTION

Natural rubber is a polymer, which is initiated by an allylic diphosphate molecule and extended by sequential addition of hundreds or thousands of molecules of isopentenyl diphosphate. In guayule, this polymerization occurs within the parenchyma cells of the bark (Backhaus, 1985). The enzyme which catalyzes this biosynthesis is called rubber transferase (Cornish, Castillón and Chapman, 1998) and is found in the lipid monolayer surrounding cytosolic rubber particles (Cornish, Wood and Windle, 1999). The activity of rubber transferase is induced in late October and early November during the year (Cornish and Siler, 1996); this results in the accumulation of rubber particles in guayule branches and stems during the winter. Guayule rubber latex results from the suspension of rubber particles collected by centrifugation of the extracts obtained by homogenizing guayule bark in aqueous solvents.

Figure 1:
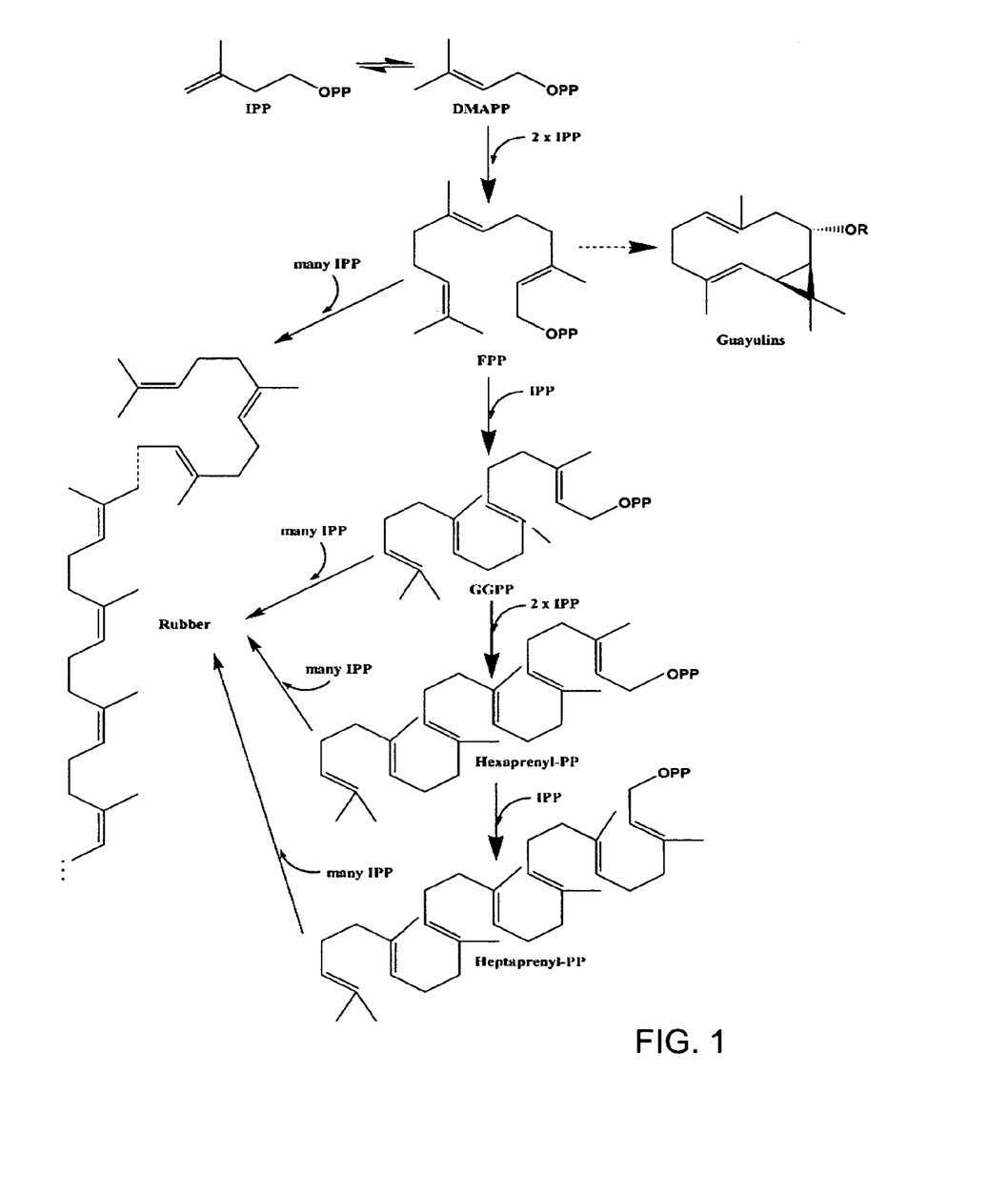

Rubber transferase catalyzes the addition of thousands of isopentenyl diphosphate (IPP) molecules to a single initiator molecule to yield a polyisoprene molecule commonly referred to as rubber (Cornish, Castillón and Chapman, 1998). The enzyme requires an allylic diphosphate as the initiator substrate, IPP, as the elongating substrate and Mg++ as a cofactor. The enzyme has a pH optimum of 7.8 and is optimally active at 16° C. FIG. 1 depicts overall rubber synthesis, which includes the allylic diphosphate intermediates.

The initiator for a single molecule of rubber is categorized as an allylic diphosphate, which includes molecules such as dimethylallyl diphosphate, geranyl diphosphate, farnesyl diphosphate, geranylgeranyl diphosphate, geranylfarnesyl diphosphate, hexaprenyl diphosphate, heptaprenyl diphosphate, octaprenyl diphosphate, and solanesyl diphosphate.

In vitro studies have suggested that increasing the amount of allylic diphosphate initiator molecules available to rubber transferase should result in higher rates of rubber synthesis if IPP is not limiting to the enzyme (Castillon and Cornish 43-51). The results presented here show that the constituents of guayule latex and its byproducts are indeed favorably affected by manipulating the reference initiator molecules.

In vitro experiments measuring the rate of rubber initiation by the *P. argentatum* rubber transferase have shown that the enzyme used allylic diphosphate initiators with increasing efficiency up to a length of FPP (Cornish and Siler 301-05), but the enzyme is able to use longer initiators (Archer and Audley 181-96; Cornish, Castillon, and Chapman 316-23). However, other cytoplasmic processes compete with the rubber transferase for FPP, such as sterol and resin biosynthesis. Therefore, genes encoding microbial enzymes synthesizing GGPP and a mixture of hexa-/heptaprenyl diphosphates were also transformed into guayule to determine the effects of providing alternate allylic diphosphate initiators for rubber synthesis without the ability to be consumed by alternate reactions.

Manipulating the concentration of allylic diphosphates within the *P. argentatum* cell results in transgenic plants with decreased levels of possible rubber contaminants such as guayulins, or with variable levels of resin which can have industrial uses.

Lower concentrations of guayulins reduce the level of compounds that have been reported to cause dermatitis in guayule-derived natural rubber products. (Rodriquez, et. al. 1981). Increased resin content would be useful because the resin extract from guayule or guayule bagasse has value in many industrial applications such as, but not limited to, coatings and adhesives. Increased resin content also would be useful in the bagasse, which is envisioned as a raw material for particle board. Bagasse is the residual chipped woody material from guayule stems and branches leftover after aqueous extraction of the rubber particles out of these chips. Current particle board formulation requires the addition of resins to the mixture of wood chips; wood chips already containing a high level of resin would result in cheaper costs for manufacturers.

The manipulation of allylic diphosphate levels, therefore, has an impact on industrial products. For example, transgenic guayule lines may be engineered to produce rubber content with enhanced flexibility and strength. Additionally, transgenic guayule may be produced that evinces lower contaminants such as guayulins or different levels of resin which can be used to produce various industrial products.

In order to manipulate the allylic disphosphate levels in guayule, *Agrobacterium*-mediated transformation can be applied by using the modified protocol of Pan et al. (Pan et al. 143-50). Control plants can be transformed with binary vectors lacking any allylic diphosphate synthase transgene but containing the NPTII selectable marker gene. Transformed shoots can be selected using kanamycin, and the surviving Shoots can be rooted (Castillón and Cornish 215-19), checked for the presence of the transgene by PCR, and then transplanted into the field. Other methods of transformation, such as using leaf discs, may also be used. Examples of how this procedure may be implemented are set forth below.

EXAMPLES

The following examples are not intended to limit the scope of the invention but to instead merely provide illustrative uses.

In general, the manipulation of allylic diphosphate levels has led to the creation of various transgenic guayule lines that provide the following advantages or attributes: reduced guayulin content for use in the manufacture of medical rubber products with decreased risks of dermatitis; and enhanced resin content for use in various industrial applications such as, but not limited to, chipped bark and stem material in the construction of particle board, an application which requires less resin added than the normal manufacturing process because of the inherent resin levels contained in the guayule material; enhanced extractable resin yields with value and application in the paper, coatings, and adhesive industries and as a substitute for pine resin. Some transgenic guayule lines also produce smaller rubber particles with reduced molecular weight, which give certain manufacturing advantages.

These advances were achieved by producing transgenic lines of guayule, *Parthenium argentatum* Gray, which were transformed using constitutively expressed transgenes encoding allylic diphosphate synthases. This was done through *Agrobacterium*-mediated transformation, followed by field trials. Details of these procedures are set forth below.

STATEMENT OF DEPOSIT

Biologically pure cultures of E. Coli, strains pCM1, pCM3, and pCM4, were deposited on Dec. 15, 2004 under terms of the Budapest Treaty with the Agricultural Research Service Culture Collection (NRRL), National Center for Agricultural Utilization Research, USDA, 1815 N. University Street, Peoria, Ill. 61604. The strains were given the respective accession numbers of NRRL B-30799, NRRL B-30800, and NRRL B-30801. For the purposes of this invention, any isolate having the identifying characteristics of these respective strains, including subcultures and variants thereof which have the identifying characteristics and activity as described herein, are included.

Preparation of the Transgene Constructs

Several transgene constructs were identified and prepared in order to carry out the experiments set forth below: pCM1 increases the expression of FPP synthase, which makes FPP; pCM3 increases the expression of GGPP synthase, which makes GGPP; and pCM4 increases the expression of a mutant GGPP synthase, which makes a mixture of hexa- and heptaprenyl diphosphate. (Ohnuma et al., 1996).

Construction of pCM1. pBS FPPS containing the FPP synthase from *Bacillus stearothermophilus* (Genbank accession number D13293) (Koyama et al. 355-63) was digested with NcoI and HindIII to release the FPP synthase cDNA sequence from the pTV118N vector. This cDNA sequence was ligated into pLITMUS29 digested with NcoI and HindIII in order to introduce a BamHI site 3' to the coding region of the cDNA. The resulting construct was digested with NcoI and BamHI to release the modified FPP synthase cDNA (with a 5' NcoI and 3' BamHI restriction site) and inserted between the CaMV 35S promoter and the octopine synthase 3' terminator of the pSLJ4D4 vector (Jones et al. 285-97) digested with NcoI and BamHI. This ligation placed the modified FPP synthase cDNA under the regulation of the CaMV 35S promoter (resulting in constitutive expression) and terminating the mRNA being transcribed from this 35S promoter at the octopine synthase 3' terminator sequence.

The resulting construct (FPS/pSLJ4D4 #1) was verified by restriction mapping and DNA sequencing of the junctions to ensure that the desired translational fusion was made. To insert the transgene into the disarmed binary plant transformation vector pCGN1547, FPS/pSLJ4D4 #1 was digested with BglII and partially digested by HindIII to release the CaMV 35S promoter-FPP synthase-ocs 3' fragment for ligation into the pCGN1547 vector (McBride and Summerfelt, 1990) digested with BamHI and HindIII. This construct (pCM1) contained the neomycin phosphotransferase (NPTII) selectable marker gene (driven by the mannopine synthase [mas] promoter and terminated by the mas 3' terminator) and the CaMV 35S promoter-FPP synthase-ocs 3' fusion, which were both flanked by the right and left T-DNA borders. This binary plasmid contained the transgene closest to the right T-DNA border to ensure that the T-DNA transferred to the plant received the transgene before the NPTII selectable marker gene was transferred. Thus, any kanamycin-resistant plants should also have inserted the recombinant FPP synthase gene.

Construction of pCM3. pGGPPS containing the GGPP synthase from *Sulfolobus acidocaldarius* (Genbank accession number D28748) (Ohnuma, et al., 1994) was digested with BamHI and XhoI to release the GGPP synthase cDNA from pBluescript KS+. This insert was ligated into pLITMUS29-derivative containing the ocs 3' fragment cloned into the BamHI and Hindi sites (with the BamHI being the 5'end) digested with BamHI and XhoI in order to place the ocs 3' region downstream of the cDNA. The resulting construct was digested with KpnI and partially digested with BamHI and inserted 3' of the potato UBI3 promoter (from pUbi3-GUS plasmid described in (Garbarino and Belknap, 1994)) digested with BamHI and KpnI. This ligation placed the GGPP synthase cDNA under the regulation of the potato ubi3 promoter (resulting in constitutive expression) and terminating the mRNA being transcribed from this ubi3 promoter at the octopine synthase 3' terminator sequence.

The resulting construct (pUBI3-GGPPS-ocs) was verified by restriction mapping and DNA sequencing of the junctions to ensure that the desired translational fusion was made. To insert the transgene into the disarmed binary plant transformation vector pCGN1547, pUBI3-GGPPS-ocs was digested with KpnI and partially digested by BamHI to release the potato UBI3 promoter-GGPP synthase-ocs 3' fragment for ligation into the pCGN1547 vector digested with BamHI and KpnI. This construct (pCM3) contained the neomycin phosphotransferase (NPTII) selectable marker gene (driven by the mannopine synthase (mas) promoter and terminated by the mas 3') and the potato UBI3 promoter-GGPP synthase-ocs 3' fusion, which were both flanked by the right and left T-DNA borders. This binary plasmid contained the transgene closest to the right T-DNA border to ensure that the T-DNA transferred to the plant received the transgene before the NPTII selectable marker gene was transferred. Thus, any kanamycin-resistant plants should also have inserted the recombinant GGPP synthase gene.

Construction of pCM4. pGGPPS containing the GGPP synthase from *Sulfolobus acidocaldarius* (Genbank accession number D28748) (Ohnuma, Suzuki, and Nishino 14792-97) was digested with BamHI and XhoI to release the GGPP synthase cDNA from pBluescript KS+. This insert was ligated into pLITMUS29-derivative containing the ocs 3' fragment cloned into the BamHI and HindIII sites (with the BamHI being the 5'end) digested with BamHI and XhoI in order to place the ocs 3' region downstream of the cDNA. The resulting construct was digested with KpnI and partially digested with BamHI and inserted 3' of the potato UBI3 promoter (from pUbi3-GUS plasmid described in (Garbarino and Belknap, 1994) digested with BamHI and KpnI. This ligation placed the mutant GGPP synthase cDNA under the regulation of the potato ubi3 promoter (resulting in constitutive expression) and terminating mRNA being transcribed from this ubi3 promoter at the octopine 3' terminator sequence.

This resulting construct (pUBI3-L4-ocs) was verified by restriction mapping and DNA sequencing of the junctions to ensure that the desired translational fusion was made. To insert the transgene into the disarmed binary plant transformation vector pCGN1547, pUBI3-L4-ocs was manipulated in the same fashion as for pCM3. This construct (pCM4) construct contained the neomycin phosphotransferase (NPTII) selectable marker gene (driven by the mannopine synthase (mas) promoter and terminated by the mas 3') and the potato UBI3 promoter-L4 mutant GGPP synthase-ocs 3' fusion, which were both flanked by the right and left T-DNA borders. This binary plasmid contained the transgene closest to the right T-DNA border to ensure that the T-DNA transferred to the plant received the transgene before the NPTII selectable marker gene was transferred. Thus, any kanamycin-resistant plants should have also inserted the recombinant GGPP synthase gene.

Transformation

The transformation procedure which was followed is that which was outlined in general by Pan (Pan et al., 1996). *Agrobacterium*-mediated transformation using leaf disc explants has also proven useful. For these transformation procedures, a 5 mL culture of *Agrobacterium tumefaciens* strain LBA4404 harboring the desired binary plasmid was started by inoculating Luria-Bertani (LB) broth supplemented with 10 µg/mL kanamycin. Fresh *Agrobacterium* cultures (25 mL) were created by making a 1/25th dilution in LB broth plus 10 µg/mL kanamycin and incubated with shaking at 200 rpm for 2 days at 27° C. in Luria-Bertani broth media (pH 7) containing 10 µg/mL kanamycin. On the day of transformation, 0.1M acetosyringone (dissolved in DMSO) was added to the media at a final concentration of 100 µM, and the culture was incubated as before for at least another 4 hours. The *Agrobacterium* cells were pelleted by centrifugation and resuspended in 1× Murashige-Skoog liquid salts (Invitrogen Corporation, Carlsbad, Calif., USA) at a final concentration of $10^{10}$ cells/mL.

The axillary meristematic regions of tissue-cultured guayule shoots from parent lines (see drawing descriptions to identify particular parent lines) were inoculated with the suspension of *Agrobacterium* cells using a syringe with a 25 gauge hypodermic needle. (Castillon and Cornish, 2000). The shoots were grown in tissue culture media supplemented with 100 µg/mL carbenicillin and 50 µg/mL kanamycin for 4-5 weeks before being transferred to fresh medium. The *Agro-* bacterium-infected shoots were propagated on carbenicillin and kanamycin for three 4-week periods before being grown on kanamycin only.

The transformed shoots were rooted in Sorbarod cellulose plugs (Sigma Chemical Company, St. Louis, Mo., USA) (Castillon and Cornish, 2000) soaked in tissue culture medium containing 50 µg/mL kanamycin. When roots were just emerging from the bottom, the plants and Sorbarod plugs were transplanted into cactus mix potting medium (Uni-Gro Cactus Mix, L&L Nursery Supply, Chino, Calif., USA) using specialized pots (Rootrainer, Spencer-Lemaire Industries, Ltd., Edmonton, Alberta, Canada) in a greenhouse. After watering the trays, the plants were covered with a translucent plastic tent for one week with frequent watering. The tent was then removed, and the plants were watered daily for one week and three times a week thereafter. The greenhouse temperature was kept between 14° C. and 30° C. After several weeks, the plants were planted in the field.

Field Tests

The guayule plant lines transformed pursuant to the above-referenced protocols were grown in the greenhouse for 3 months before being transplanted into field plots at Maricopa Agricultural Center of the University of Arizona and maintained for a period of two years. No fertilizer was added, and the field was irrigated every 14 d from March until October and every 42 d from October to March. The plants from these field trials were harvested and then subjected to the following protocol.

Resin and rubber were quantified by gravimetric analysis of solvent-extracted guayule branches (Black et al., 1983). For each measurement, one or two branches of each plant were dried at 80° C. for 2 days; the branches were then homogenized in a coffee grinder and extracted with acetone to measure resin content or extracted with cyclohexane to determine rubber content. The fresh weight was recorded at time of harvest, and the dry weight was obtained after drying the ground material at 100° C. for 2 days. The resin and rubber yields per plant were calculated as the percent resin or rubber per dry weight of the plant.

Following harvesting, each plant line was analyzed for the following criteria: rubber prenyltransferase activity, guayulin content, resin content, latex yield, and rubber content.

Prenyltransferase Activity

Figure 2A:
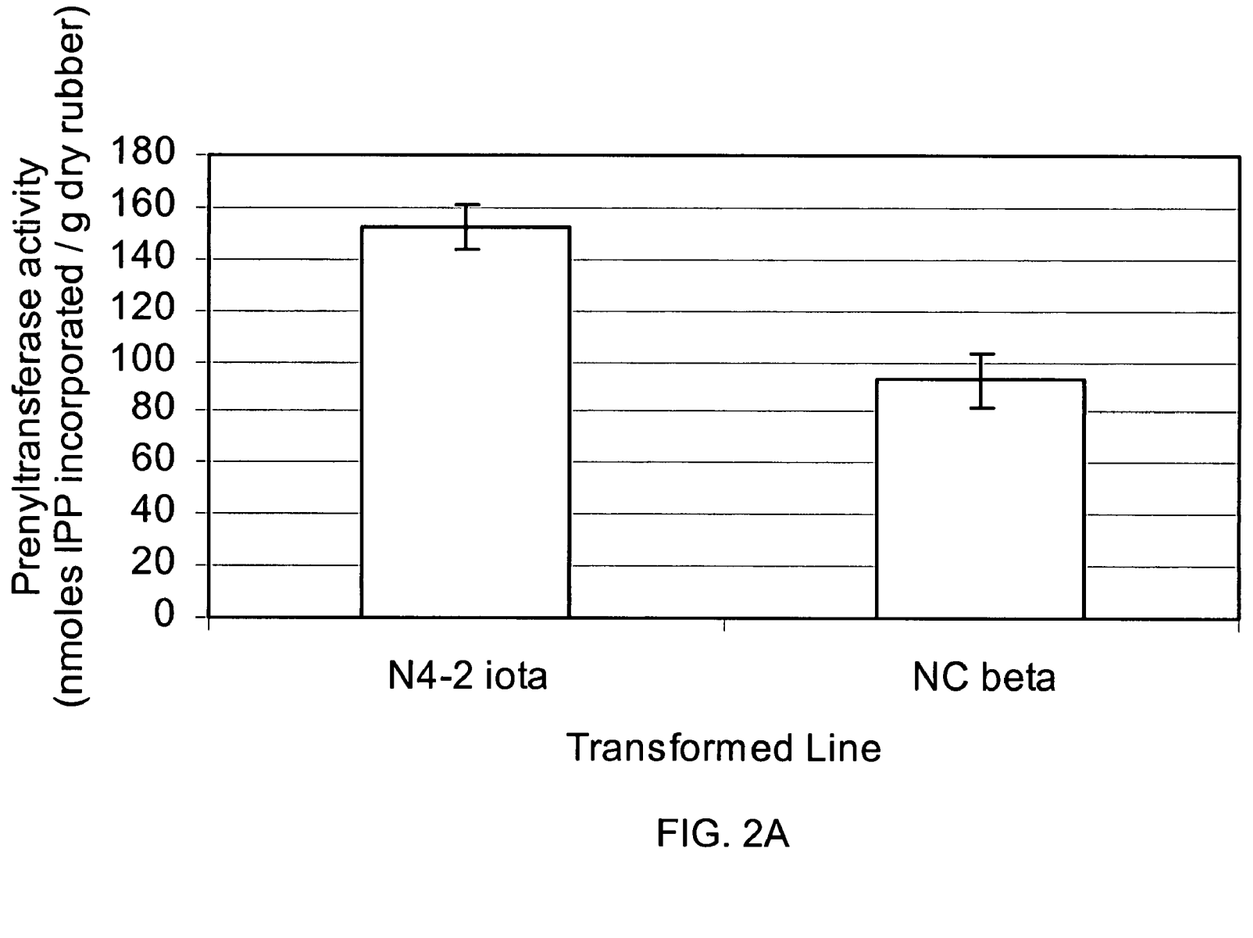
FIG. 2A and FIG. 2B show prenyltransferase activity among different lines of *Parthenium argentatum* transformants after two years in the field.
Figure 2B:
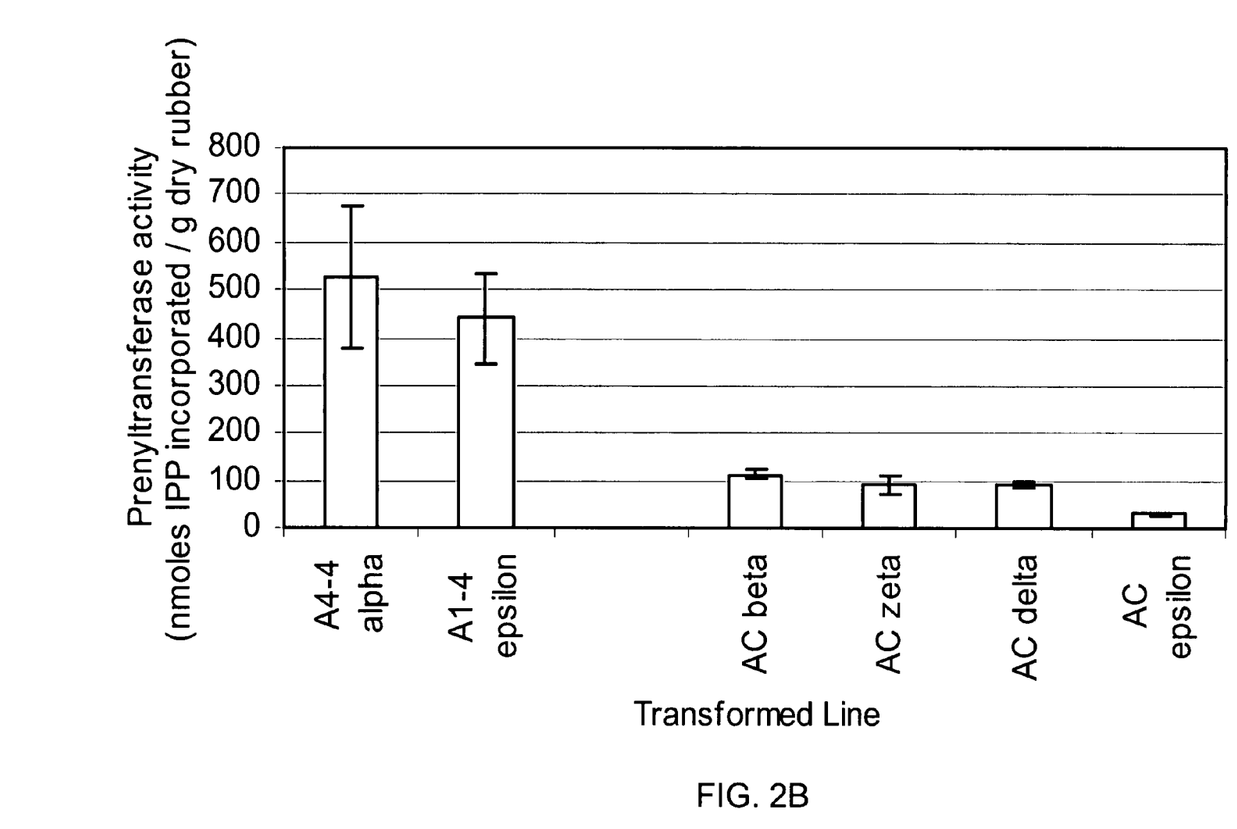
Figure 3A:
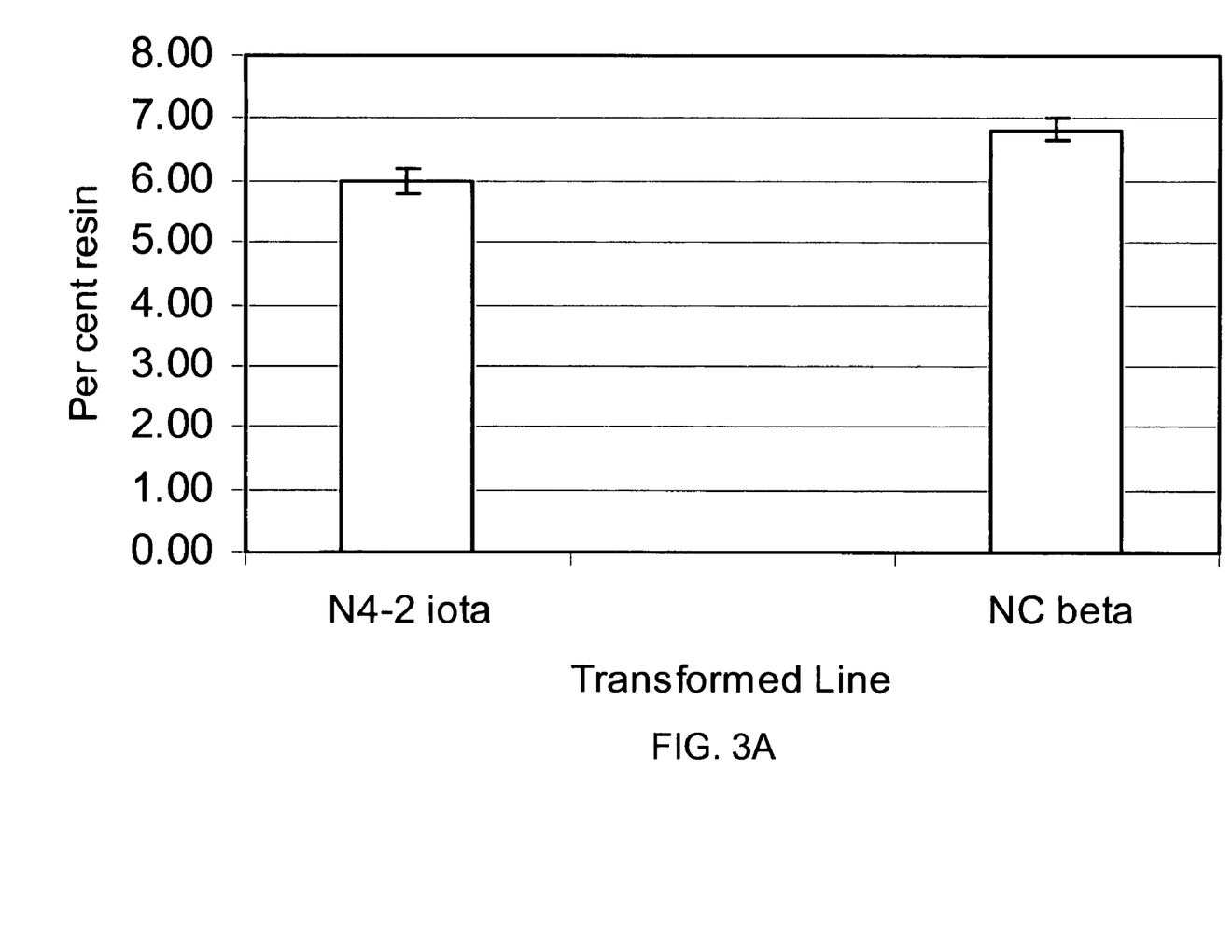
FIG. 3A and FIG. 3B show percent resin production in various lines of transformed guayule.
Figure 3B:
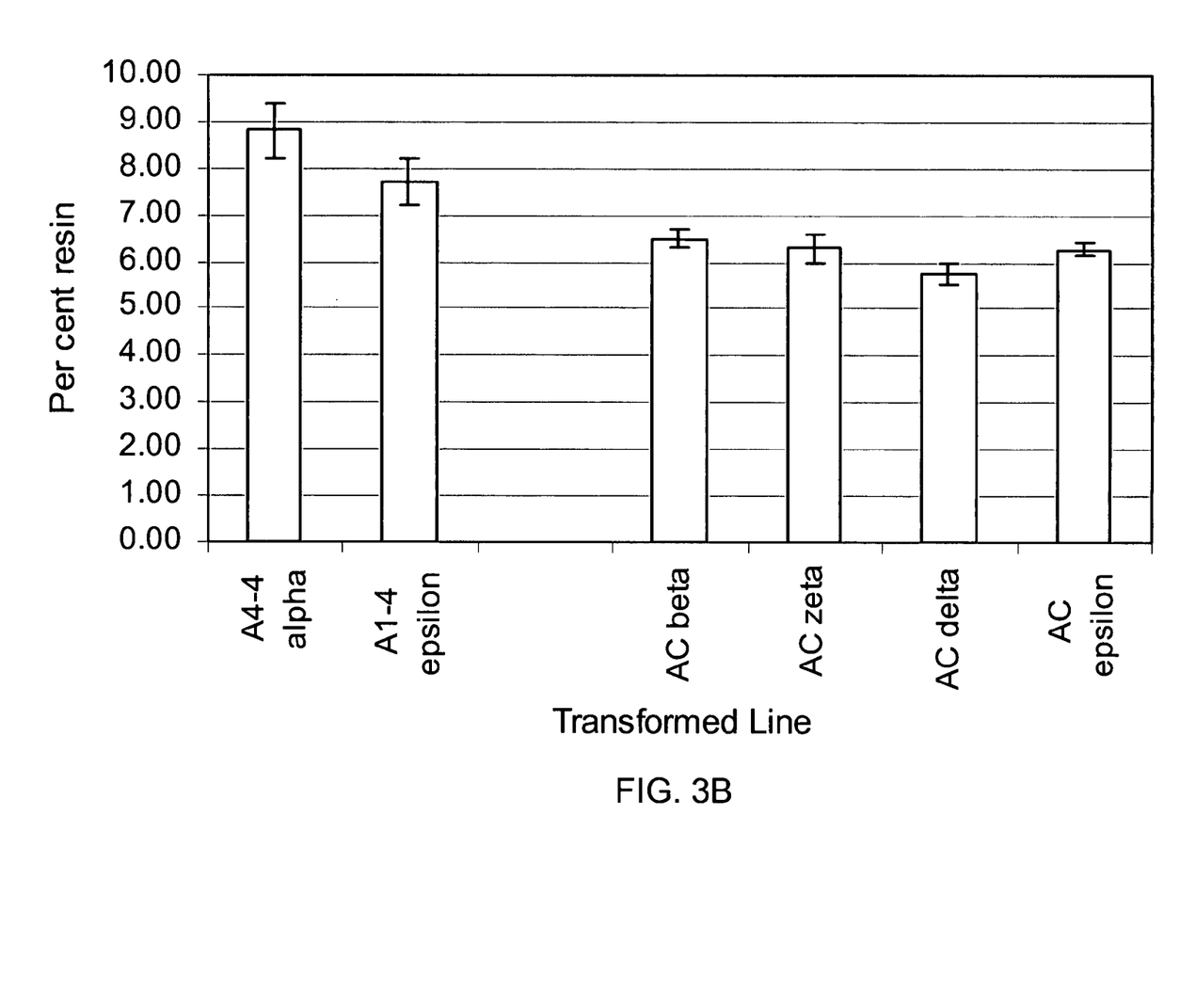

After the second year of growth in the field, various trends were noted in respect to prenyltransferase activity. For example, the transformed clones in general showed elevated prenyltransferase activity above the controls (FIGS. 2A and 2B). Some lines showed as much as 4 to 5 times more prenyltransferase activity than that seen in the controls.

The increase in the prenyltransferase activity is significant because in vitro experiments have demonstrated that the rate of rubber biosynthesis increases when the rubber transferase is incubated with longer allylic diphosphate initiators in the presence of non-limiting IPP (Cornish and Siler, 1995). These plants represent the in vivo extension of these biochemical studies. In addition, the results from these transgenic plants suggest that providing the rubber transferase with an allylic diphosphate initiator that is not normally present in the cytosol leads to the sequestration of newly-synthesized rubber into a form not extractable by aqueous solvents. The results from these plants also suggest that the utilization of transgene-produced foreign allylic diphosphates by the rubber transferase may allow more FPP to be incorporated into resin components by removing a sink for FPP; active rubber transferase can use other allylic diphosphate initiators instead of FPP.

Guayulin Production

The manipulation of the expression of prenyltransferase and allylic diphosphate molecules can be utilized to influence the production of guayulins, components of plant resin that can cause dermatitis in some people (Rodriquez et. al. 1981).

Figure 4A:
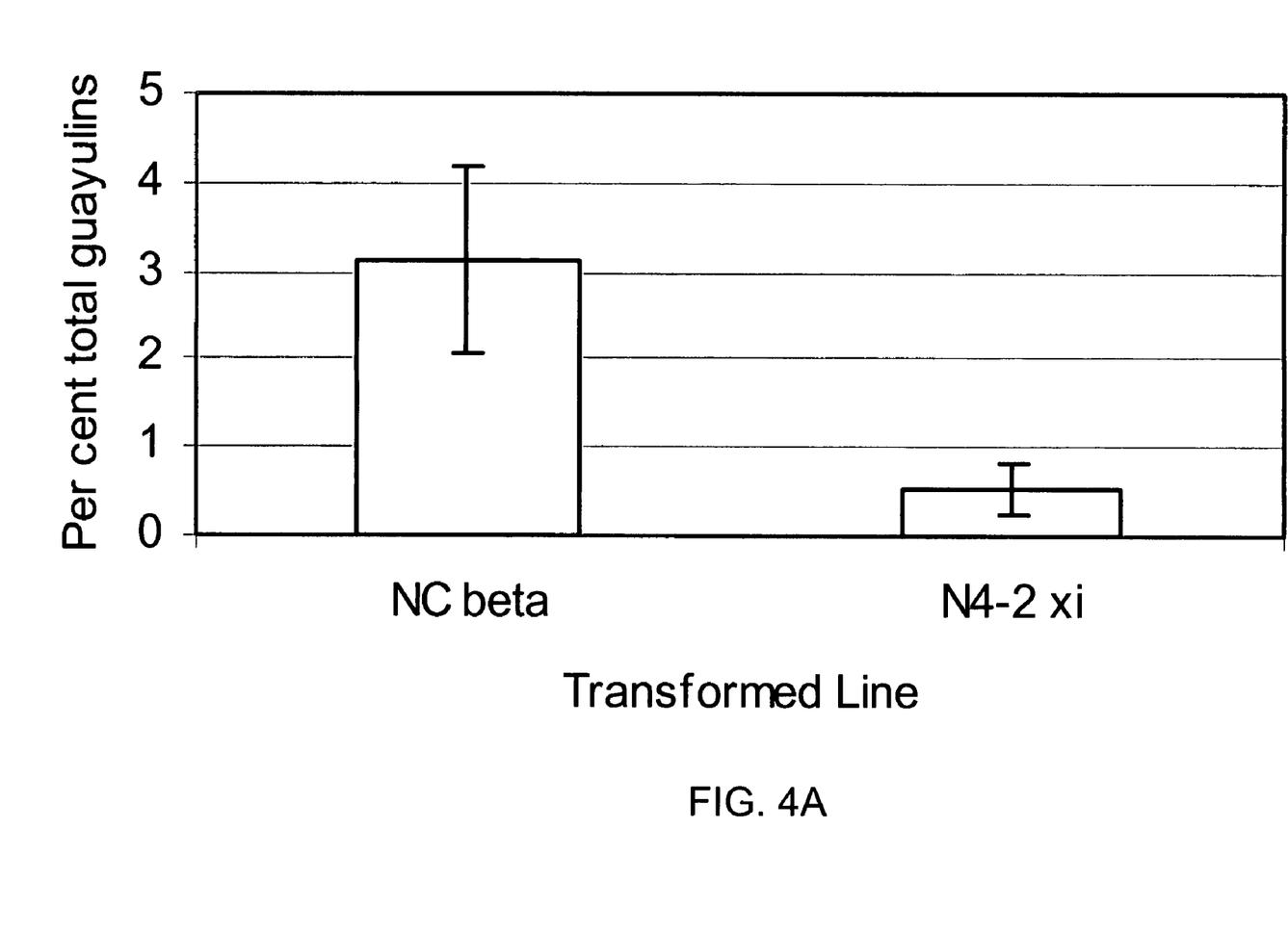
FIG. 4A, FIG. 4B, and FIG. 4C show percent guayulin production in various lines of transformed guayule. In all three cases, the transformed line N4-2 xi is compared to the control line NC beta.
Figure 4B:
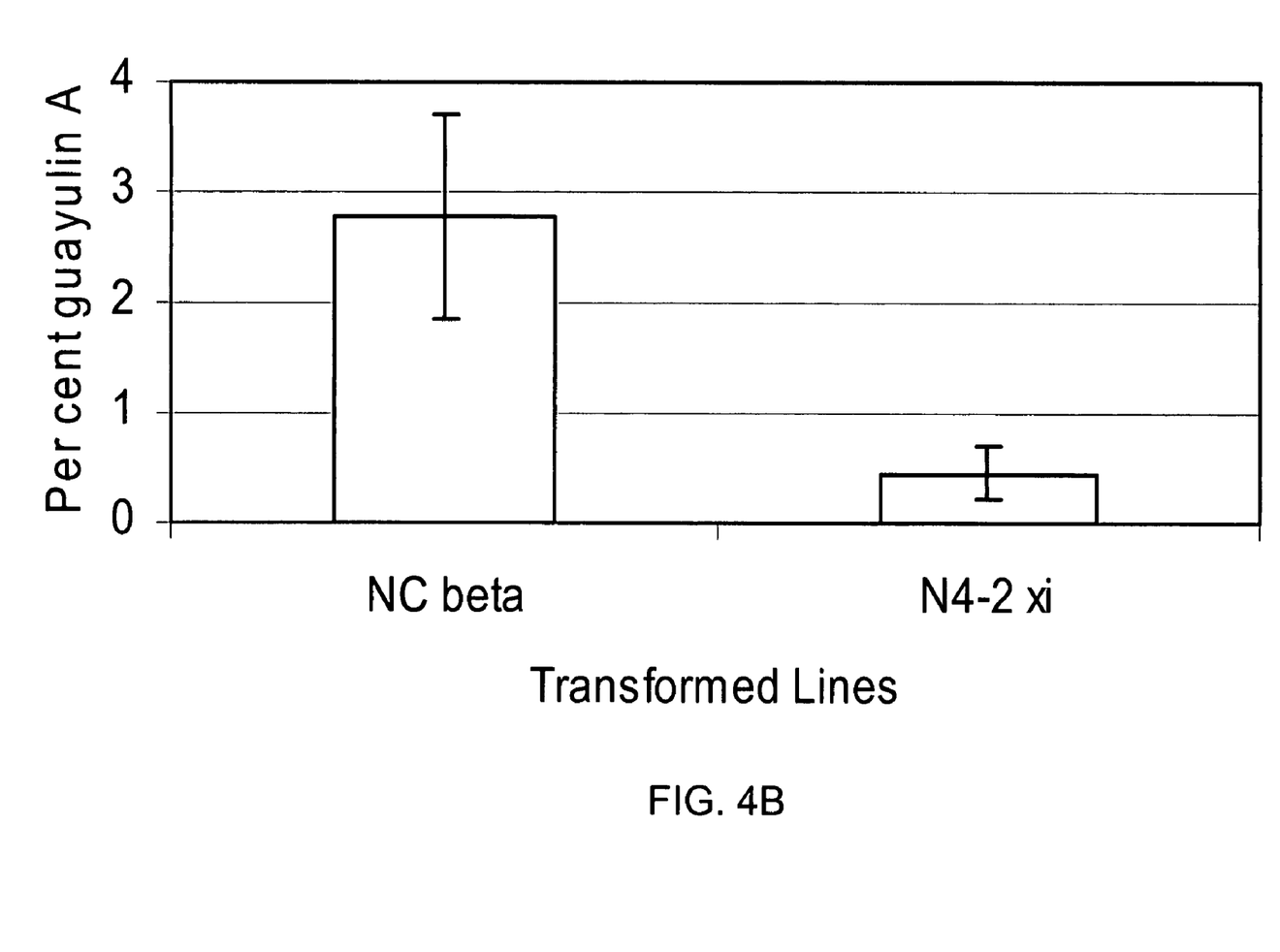
Figure 4C:
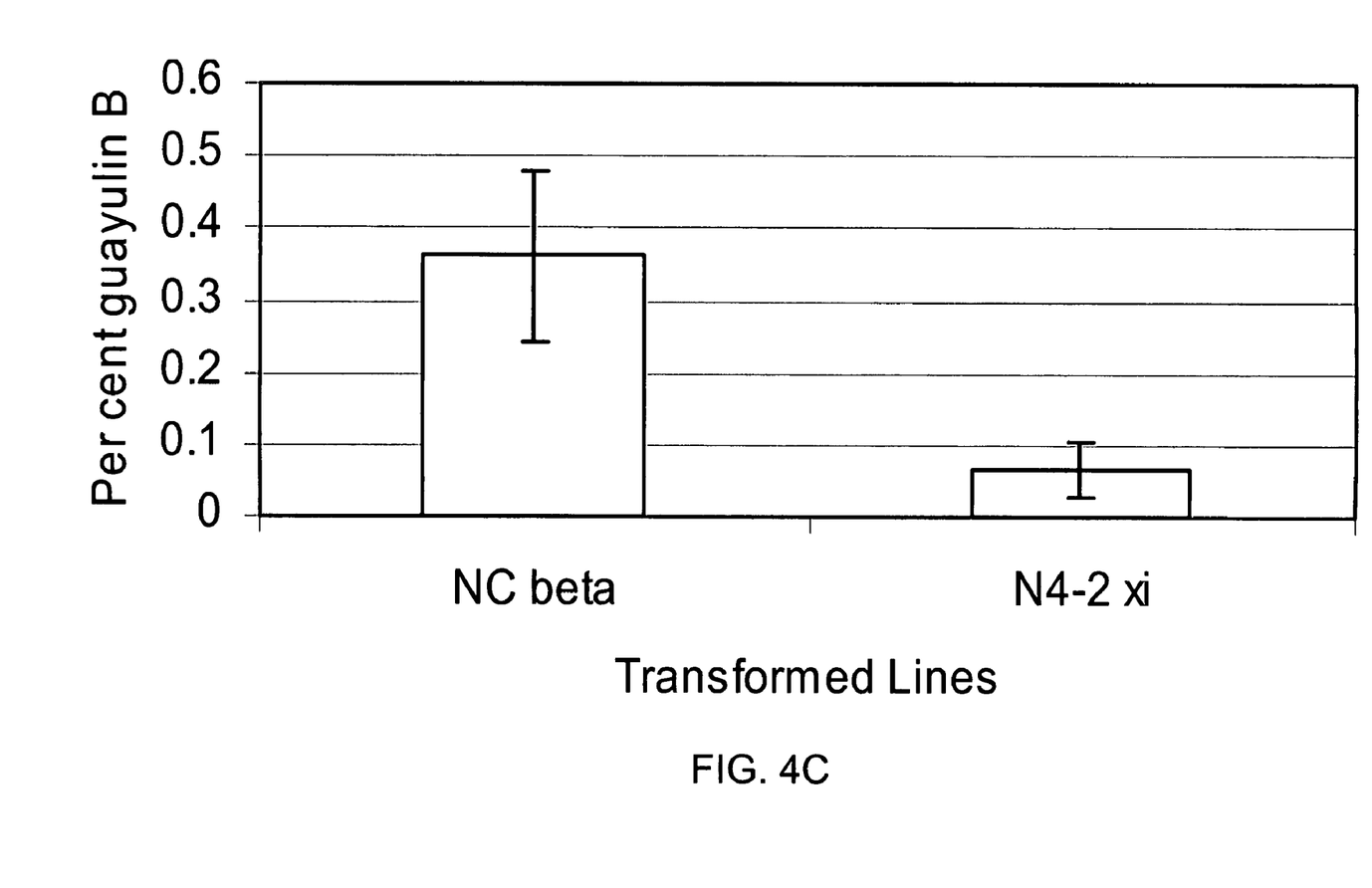

The guayulin content of the transformants was also measured and compared to the controls. See FIGS. 4A-C. For the line N4-2 xi, the total guayulin, guayulin A and guayulin B levels were decreased compared to control NC beta plants. This line would be useful in producing natural rubber products containing lower guayulin contamination. These products would be valuable to anyone desiring reduced-allergen latex products Resin Production The resin levels found in the transgenic plants also showed a correlation to prenyltransferase activity. For example, transgenic lines N4-2 xi had statistically significant reduced levels of resin compared to the control plants, while transgenic lines A1-4 epsilon and A4-4 alpha had statistically significant elevated levels of resin when compared to the control plants. Thus, depending on the desires of the growers, the N4-2 xi transgenic lines can be planted to yield guayule crops for producing natural rubber with lower resin contamination than normal guayule, and the A1-4 epsilon and A4-4 alpha transgenic plants can be grown to produce guayule with higher resin content would be useful for the manufacturing of such products as particle board which is generally produced from chipped wood material that is leftover from the aqueous extraction of rubber particles. Current manufacturing of particle board includes the addition of resin to the chipped wood material being used.

Rubber Particle Size

Figure 5:
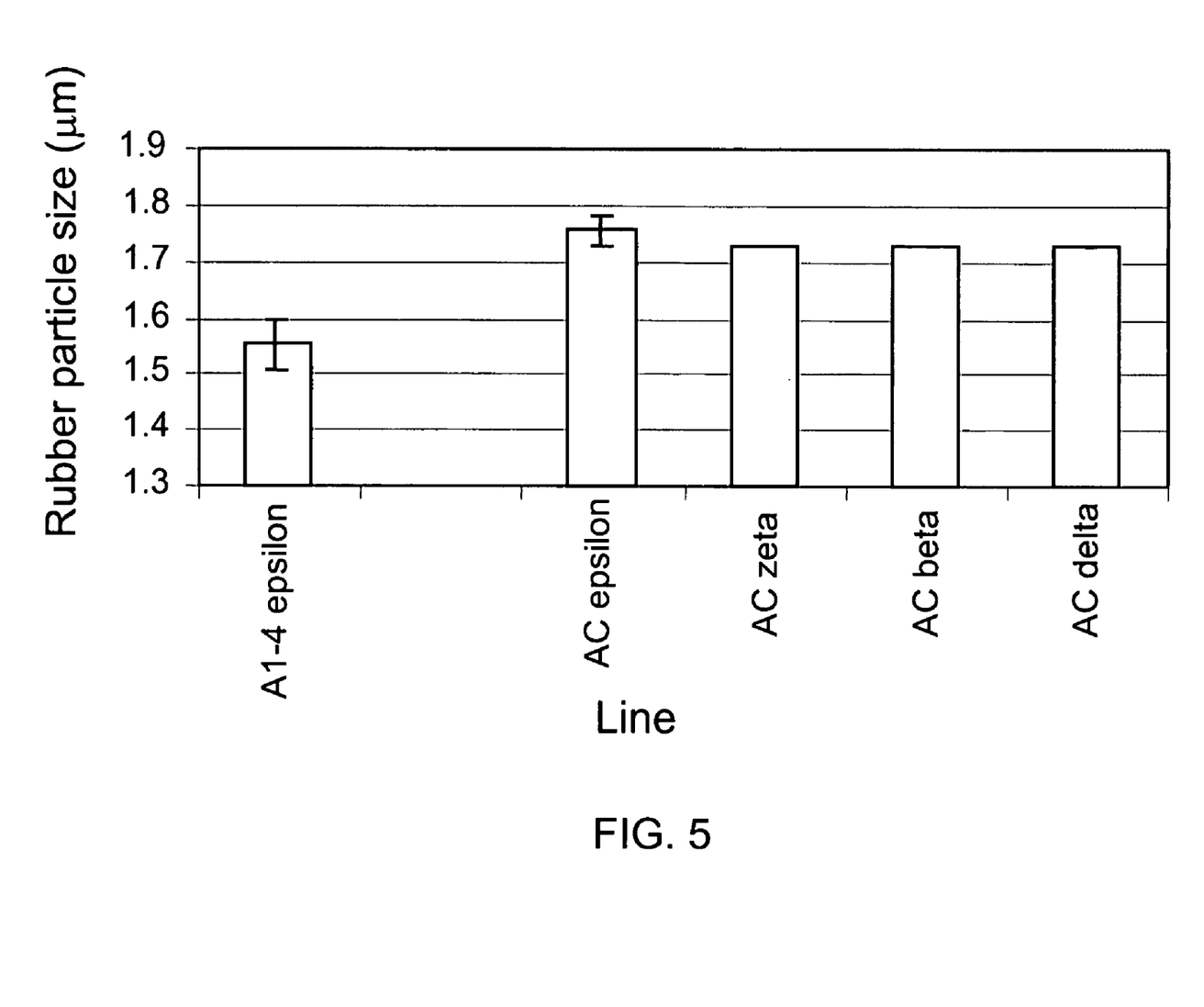
FIG. 5 shows a comparison of the rubber particle size of the transformed line A1-4 epsilon with those from the transformed control lines AC beta, delta, epsilon and zeta.

Rubber particle size and their number may also be affected by enhancing prenyltransferase activity. For example, transformed line A1-4 epsilon showed a reduction in the size of an average rubber particle being produced by the plant when compared to the transformed contro lines AC beta, AC delta, AC epsilon and AC zeta (FIG. 5). Moreover, lines transformed with farnesyl diphosphate synthase demonstrated an inverse correlation of activity and molecular weight not matched by a concomitant drop in rubber and latex yield, indicating the presence of physically more but lower molecular weight molecules.

Number of Rubber Molecules Made

Figure 6A:
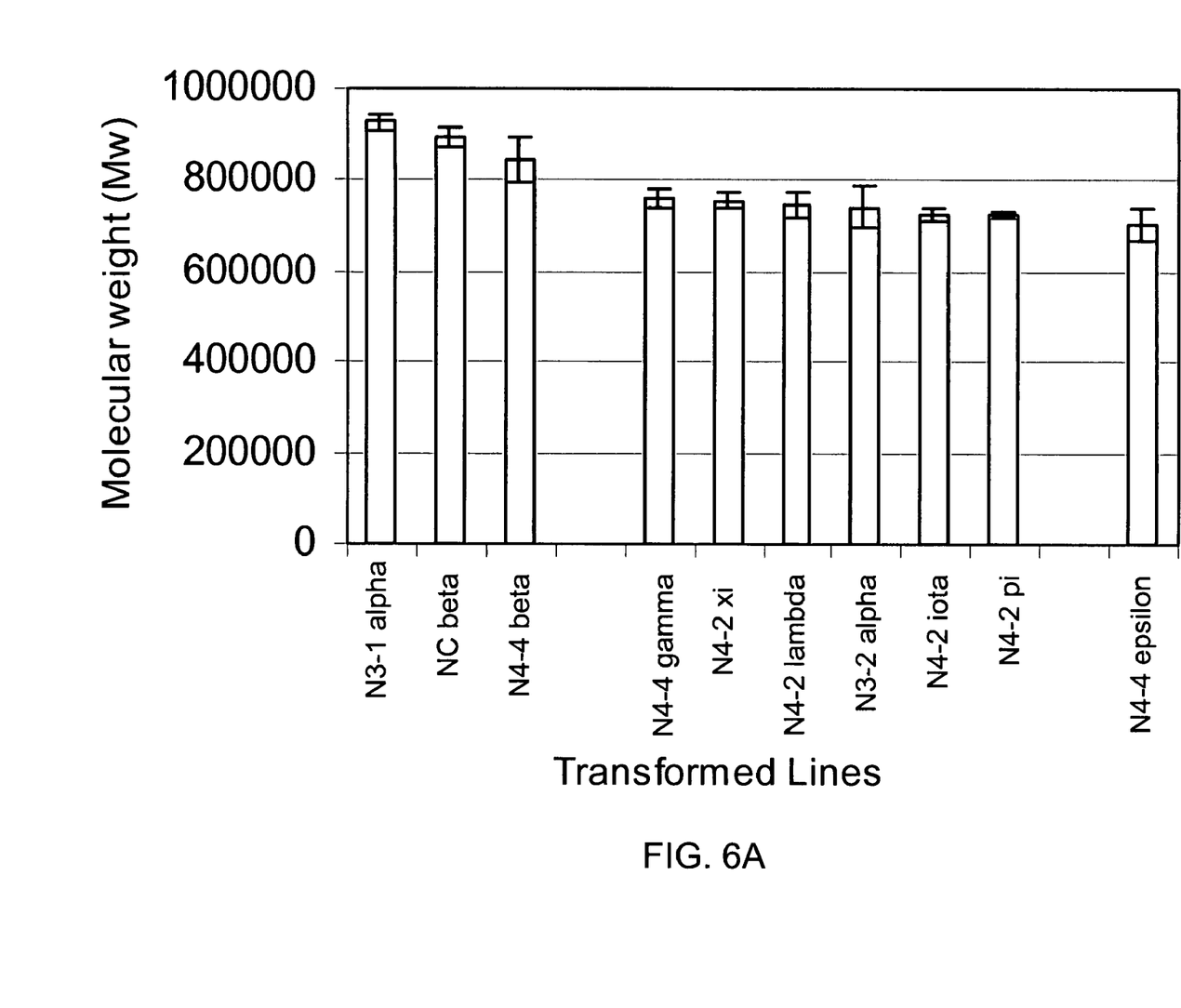
FIG. 6A and FIG. 6B show the Mw molecular weight of the rubber produced and the total rubber (extractable by cyclohexane) produced in various lines of transformed guayule. In both figures, the transformed lines N3-1 alpha, N3-2 alpha, N4-2 iota, N4-2 lambda, N4-2 xi, N4-2 pi, N4-4 beta, N4-4 gamma and N4-4 epsilon are compared to the control line NC beta.
Figure 6B:
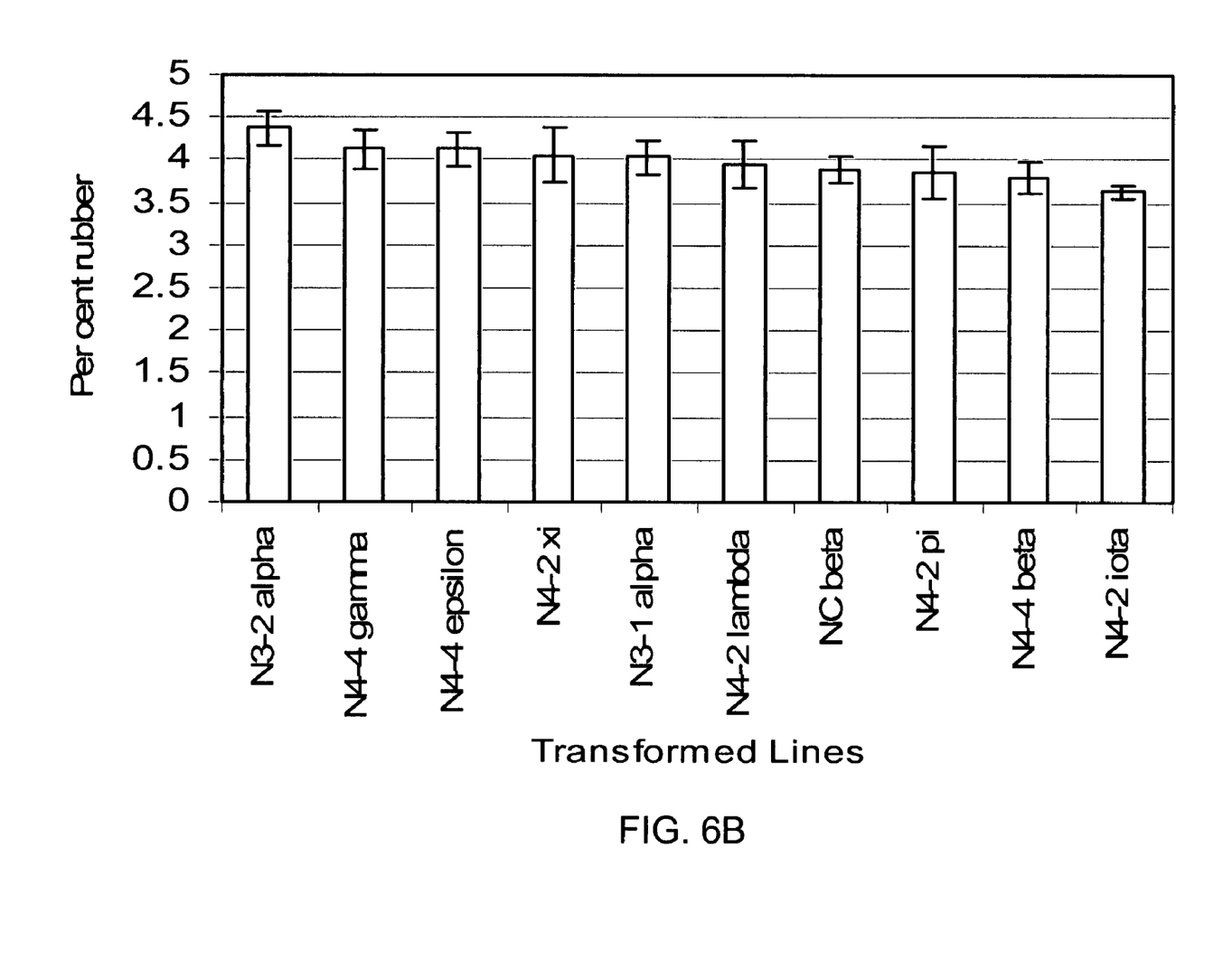

The elevated prenyltransferase activity in the transformed lines N3-1 alpha, N3-2 alpha, N4-2 iota, N4-2 lambda, N4-2 xi, N4-2 pi, N4-4 beta, N4-4 gamma and N4-4 epsilon (FIG. 2A) resulted in an increase in the number of rubber molecules made compared to the number made by the control line NC beta. The transformed lines N3-1 alpha, N3-2 alpha, N4-2 iota, N4-2 lambda, N4-2 xi, N4-2 pi, N4-4 beta, N4-4 gamma and N4-4 epsilon had a population of rubber molecules which were shorter in length compared to the control line NC beta (FIG. 6A), but made a higher number of rubber molecules such that the total amount of solvent-extractable rubber was equal to that produced in the control line NC beta (FIG. 6B). Making more of the shorter rubber molecules was the only way to accomplish this. These lines would be useful to researchers and manufacturers who wanted increase the amount of rubber molecules as an initial step to increase the rubber yield of the guayule crop.

REFERENCES

Archer, Bernard L. and Brian G. Audley. "New aspects of rubber biosynthesis." Botanical Journal of the Linnean Society 1987: 181-96.

Backhaus, Ralph A. "Rubber formation in plants—a mini-review." Israel Journal of Botany 1985: 283-93.

Carey, Andrew B. et al. "Cross-reactivity of alternate plant sources of latex in subjects with systemic IgE-mediated sensitivity to *Hevea brasiliensis* latex." Annals of Allergy Asthma and Immunology 1995: 317-20.

Castillon, Javier and Katrina Cornish. "Regulation of initiation and polymer molecular weight of cis-1,4-polyisoprene synthesized in vitro by particles isolated from *Parthenium argentatum*." Phytochemistry 1999: 43-51.

Castillón, Javier and Katrina Cornish. "A simplified protocol for micropropagation of guayule (*Parthenium argentatum* Gray)." In Vitro Cellular and Developmental Biology 2000: 215-19.

Cornish, Katrina. "Biochemistry of natural rubber, a vital raw material, emphasizing biosynthetic rate, molecular weight and compartmentalization, in evolutionarily divergent plant species." Natural Product Reports 2001: 182-89.

Cornish, Katrina and Ralph A. Backhaus. "Induction of rubber transferase activity in guayule (*Parthenium argentatum* Gray) by low temperatures." Industrial Crops and Products 2003: 83-92.

Cornish, Katrina, Javier Castillon, and Mary H. Chapman. "Membrane Bound Cis-Prenyl Transferase: Regulation and Substrate Specificity." Ed. A. Steinbuchel. Weinheim: Wiley-VCH, 1998. 316-23.

Cornish, Katrina and Mary H. Chapman, Francis S. Nakayama, Stephen H. Vinyard, and Linda C. Whitehand. "Latex quantification in guayule shrub and homogenate." Industrial Crops and Products 1999: 121-36.

Cornish, Katrina and Deborah J. Siler. "Effect of different allylic diphosphates on the initiation of new rubber molecules and on cis-1,4-polyisoprene biosynthesis in guayule (*Parthenium argentatum* Gray)." Journal of Plant Physiology 1995: 301-05.

Cornish, Katrina and Deborah J. Siler. Ed. Glenn Fuller, D. D. Bills, and Thomas A. McKeon. ACS Books, 1996.

Cornish, Katrina and Siler, Deborah J. Ed. Glenn Fuller, D. D. Bills, and Thomas A. McKeon. "Advances in alternative natural rubber production," in Agricultural Materials as Renewable Resources, ACS Books, 1996.

Cornish, Katrina, Delilah F. Wood, and John J. Windle. "Rubber particles from four different species, examined by transmission electron microscopy and electron-paramagnetic-resonance spin labeling, are found to consist of a homogeneous rubber core enclosed by a contiguous, monolayer biomembrane." Planta 1999: 85-96.

Garbarino, Joan E. and William R. Belknap. "Isolation of a ubiquitin-ribosomal protein gene (ubi3) from potato and expression of its promoter in transgenic plants." Plant Molecular Biology 1994: 119-27.

Ji, W., Chauncey R. Benedict, Michael A. Foster, "Seasonal variations in rubber biosynthesis, 3-hydroxy-3methylglutaryl-coenzyme A reductase, and rubber transferase activities in *Parthenium argentatum* in the Chihuahuan desert." Plant Physiology 1993: 506-511.

Jones, Jonathan D. et al. "Effective vectors for transformation, expression of heterologous genes, and assaying transposon excision in transgenic plants." Transgenic Research 1992: 285-97.

Koyama, Tanetoshi et al. "Thermostable farnesyl diphosphate synthase of *Bacillus stearothermophilus*: molecular cloning, sequence determination, overproduction, and purification." Journal of Biochemistry 1993: 355-63.

Lloyd, Francis E. Guayule: A Rubber-Plant of the Chihuahuan Desert. Washington, D.C.: Carnegie Institute of Washington, 1911.

McBride, Kevin E. and Kristin R. Summerfelt. "Improved binary vectors for *Agrobacterium*-mediated plant transformation." Plant Molecular Biology 1990: 269-76.

Ohnuma, Shin-ichi et al. "Conversion of product specificity of archaebacterial geranylgeranyl-diphosphate synthase: identification of essential amino acid residues for chain length determination of prenyltransferase reaction." Journal of Biological Chemistry 1996: 18831-37.

Ohnuma, Shin-ichi, Manabu Suzuki, and Tokuzo Nishino. "Archaebacterial ether-linked lipid biosynthetic gene: expression cloning, sequencing and characterization of geranylgeranyl diphosphate synthase." Journal of Biological Chemistry 1994: 14792-97.

Pan, Zhiqiang et al. "*Agrobacterium*-mediated transformation and regeneration of guayule." Plant Cell, Tissue and Organ Culture 1996: 143-50.

Rodriquez, Eloy, Reynolds and Thompson, "Potent contact allergen in guayule (*Parthenium argentatum*), Science 1981: 1444-1445.

Schloman, William W., Jr. et al. "Guayule byproduct evaluation: extract characterization." Journal of Agricultural and Food Chemistry 1983: 873-76.

Siler, Deborah J., Katrina Cornish, and R. G. Hamilton. "Absence of cross-reactivity in IgE antibodies from subjects allergic to *Hevea brasiliensis* latex with a new source of natural rubber latex from guayule (*Parthenium argentatum*)." Journal of Allergy and Clinical Immunology 1996: 895-902.

We claim:

1. A transgenic guayule plant comprising a heterologous allylic diphosphate synthase, wherein the heterologous allylic diphosphate synthase is a member selected from the group consisting of an allylic diphosphate synthase encoded by an FPP synthase cDNA that comprises binary vector pCM1 from strain pCM1 that was deposited with the Agricultural Research Service Culture Collection (NRRL) and assigned accession number NRRL B-30799; a GPP synthase cDNA that comprises binary vector pCM3 from strain pCM3 that was deposited with the Agricultural Research Service Culture Collection (NRRL) and assigned accession number NRRL B-30800; an L4 mutant GPP synthase cDNA that comprises binary vector pCM4 from strain pCM4 that was deposited with the Agricultural Research Service Culture Collection (NRRL) and assigned accession number NRRL B-30801 or a combination of said members.

2. The transgenic guayule plant of claim 1, wherein the presense of the heterologous allylic diphosphate synthase results in an increased level of allylic diphosphate initiators in the transgenic guayule plant over a non-transgenic guayule plant.

3. The transgenic guayule plant of claim 1, wherein the presense of the heterologous allylic diphosphate synthase results in an increased activity of prenyltransferase in the transgenic guayule plant over a non-transgenic guayule plant.

4. The transgenic guayule plant of claim 1, wherein the presense of the heterologous allylic diphosphate synthase results in an increased level of allylic diphosphate initiators and increased activity of prenyltransferase in the transgenic guayule plant over a non-transgenic guayule plant.

5. The transgenic guayule plant of claim 1, wherein the presense of the heterologous allylic diphosphate synthase results in reduced amounts of guayulins in the transgenic guayule plant over a non-transgenic guayule plant.

6. The plant of claim 1, wherein the presense of the heterologous allylic diphosphate synthase results in increased amounts of resin in the transgenic guayule plant over a non-transgenic guayule plant.

7. The plant of claim 1, wherein the presense of the heterologous allylic diphosphate synthase results in increased production of rubber molecules in the transgenic guayule plant over a non-transgenic guayule plant.

8. A hybrid guayule plant wherein at least one parent plant is a transgenic guayule plant comprising a heterologous allylic diphosphate synthase, wherein the heterologous allylic diphosphate synthase is a member selected from the group consisting of an allylic diphosphate synthase encoded by an FPP synthase cDNA that comprises binary vector pCM1 from strain pCM1 that was deposited with the Agricultural Research Service Culture Collection (NRRL) and assigned accession number NRRL B-30799; a GPP synthase cDNA that comprises binary vector pCM3 from strain pCM3 that was deposited with the Agricultural Research Service Culture Collection (NRRL) and assigned accession number NRRL B-30800; an L4 mutant GPP synthase cDNA that comprises binary vector pCM4 from strain pCM4 that was deposited with the Agricultural Research Service Culture Collection (NRRL) and assigned accession number NRRL B-30801 or a combination of said members, and wherein said hybrid guayule plant comprises the heterologous allylic diphosphate synthase of the at least one parent plant.

9. The hybrid guayule plant of claim 8, wherein said hybrid guayule plant shows elevated prenyltransferase activity by comparison to a non-transgenic guayule plant.

10. The hybrid guayule plant of claim 8, wherein said hybrid plant underproducing underproduces guayulins by comparison to a non-transgenic guayule plant.

11. The hybrid guayule plant of claim 8, wherein the hybrid guayule plant accumulates rubber molecules and resin to a greater degree than a non-transgenic guayule plant.

12. The hybrid guayule plant of claim 8, wherein the hybrid guayule plant shows elevated levels of allylic diphosphate initiators by comparison to a non-transgenic guayule plant.

* * * * *